US00PP36956P2

(12) United States Plant Patent
Espín

(10) Patent No.: US PP36,956 P2
(45) Date of Patent: Sep. 16, 2025

(54) GRAPEVINE PLANT NAMED 'BLOMG02'

(50) Latin Name: *Vitis vinifera*
Varietal Denomination: BLOMG02

(71) Applicant: BLOOM FRESH INTERNATIONAL LIMITED, London (GB)

(72) Inventor: Juan Carreño Espín, Murcia (ES)

(73) Assignee: BLOOM FRESH INTERNATIONAL LIMITED, London (GB)

( * ) Notice: Subject to any disclaimer, the term of this patent is extended or adjusted under 35 U.S.C. 154(b) by 0 days.

(21) Appl. No.: 19/019,866

(22) Filed: Jan. 14, 2025

(51) Int. Cl.
*A01H 5/08* (2018.01)
*A01H 6/88* (2018.01)

(52) U.S. Cl.
USPC ..... Plt./207

(58) Field of Classification Search
USPC ..... Plt./205, 207
See application file for complete search history.

(56) References Cited

U.S. PATENT DOCUMENTS

PP3,106 P * 4/1972 Garabedian ..... Plt./207
PP33,449 P2 9/2021 Martinez

* cited by examiner

*Primary Examiner* — Susan McCormick Ewoldt
(74) *Attorney, Agent, or Firm* — Michael Best & Friedrich LLP

(57) ABSTRACT

'BLOMG02' is a new and distinct grapevine plant with novel characteristics that include good fertility and is tolerant to *Erysiphe necator,* which is one of the main diseases of this species. The berries produced by 'BLOMG02' are white and seedless with a crunchy texture and neutral flavor and no detectable seed traces. The berries produced by 'BLOMG02' are large, weighing 8 g/berry on average, and harvested in end of June in Murcia Region (Spain).

1 Drawing Sheet

Latin name of the genus and species: *Vitis vinifera.*
Variety denomination: 'BLOMG02'.

BACKGROUND

Described herein is a new and distinct variety of seedless grapevine named 'BLOMG02' with tolerance to *Erysiphe necator,* one of the main diseases of this specie. The new variety originated from a hybridization performed in Murcia, Spain, during 2017 between 'ITUMSIXTEEN' (U.S. Plant Pat. No. 33,449), as the pollen parent, and 'RS15-1-65' (not patented), as the seed parent. Abortive seed traces were embryo cultured and the resulting plant was planted in an evaluation block during 2018. The first evaluation of the fruit produced by 'BLOMG02' was performed during 2019. 'BLOMG02' was first asexually propagated by field grafting dormant hardwood scions to 1103 Paulsen Rootstock (not patented) in 2020 in Murcia, Spain. Fruit from the resulting four grafted 'BLOMG02' vines was first harvested in 2021. All characteristics and distinctions remain true to form and are established and transmitted through succeeding propagations.

SUMMARY

The following are the most outstanding and distinguishing characteristics of 'BLOMG02'. 'BLOMG02' produces naturally large (8 g/berry) seedless white (2.5 GY7/6) with tolerance to *Erysiphe necator.* The berries produced by 'BLOMG02' have a broad ellipsoid shape with an neutral flavor and very crunchy texture, that are harvested in end of June in Murcia-Spain.

'BLOMG02' is most similar to 'Sugraone' (U.S. Plant Patent No. 3,106). Nonetheless, the new cultivar can be distinguished from 'Sugraone' based at least upon fertility, cluster size, berry shape and berry flavor. 'BLOMG02' is tolerant to *Erysiphe necator* but 'Sugraone' is not tolerant to the main diseases of this species. 'BLOMG02' has a fertility index of 1.1 while 'Sugraone' has 0.5 fertility index. 'BLOMG02' produces berries with broad ellipsoid shape while the berries of 'Sugraone' have an ovoid shape.

'BLOMG02' can be distinguished from its male parent, 'ITUMSIXTEEN' (U.S. Plant Pat. No. 33,449), in that the harvest period of the new cultivar is in the end of June while the harvest period of 'ITUMSIXTEEN' is in the end of August. 'BLOMG02' have clusters less heavy than 'ITUMSIXTEEN' clusters (average 500 g vs. 700 g). The berries of 'BLOMG02' have a broad ellipsoid shape while the berries of 'ITUMSIXTEEN' have an obovate shape. 'BLOMG02' presents tolerance to *Erysiphe necator* and 'ITUMSIXTEEN' does not show any tolerance to any diseases of this species.

'BLOMG02' can be distinguished from its female parent, 'RS15-1-65' (not patented), in which bunch size of 'BLOMG02' is smaller (500 g) that the cluster of 'RS15-1-65' (650 g). The berries of 'BLOMG02' are seedless whereas the berries 'RS15-1-65' are seeded. The berries of 'BLOMG02' have a neutral flavor while the berries of 'RS15-1-65' have muscat flavor.

BRIEF DESCRIPTION OF THE DRAWING OR PHOTOGRAPHS

The accompanying color photographs illustrate the overall appearance of the 'BLOMG02' plant showing the colors as true as it is reasonably possible to obtain in colored reproductions of this type. Colors in the photographs may differ slightly from the color values cited in the detailed botanical description that accurately describe the colors of the plant described herein. These figures are exemplary will vary depending on the plant and distinguishing characteristics.

FIG. 1 shows the form, foliage, and fruit of a 3-year-old 'BLOMG02' vine grown in field in Murcia, Spain.

The colors shown are as true as can be reasonably obtained by conventional photographic procedures.

DETAILED BOTANICAL DESCRIPTION

The following detailed description sets forth the distinctive characteristics of 'BLOMG02'. The detailed description was obtained between March and November using 3-year-old plants grown in the field in Murcia, Spain. The color references are to the Munsell Plant Tissue Color Book, 2012 Edition by Munsell Color.

Classification:

*Family*.—Vitaceae.
*Botanical*.—*Vitis vinifera*.
*Common name*.—Grapevine.
*Cultivar name*.—'BLOMG02'.

Plant:

*Plant habit and growth*.—Semi-erect.
*Age at maturity*.—3 years old.
*Size* (*at maturity*).—Height — 225 cm. Width — 300 cm.
*Vigor*.—High.
*Productivity*.—High (1.1 fertility index), around 25 pounds/plant and 6 t/acre.
*Rootstock*.—Name of rootstock — 1103 Paulsen Rootstock (not patented). Age of rootstock at time of grafting — one year old.

Trunk:

*Size*.—Diameter — 5 cm. Height (at measured diameter of 5 cm) — 45 cm above the ground.
*Shape*.—Straight and cylindrical.
*Surface texture*.—Rough, straight grained with the outer layer easily removed.
*Bark color*.—Exterior — 7.5YR4/4. Interior — 5YR4/6.

Canes:

*Size*.—Diameter — 9.6 mm. Length — 175 cm.
*Surface texture*.—Mature cane — very smooth and very finely striated, glabrous. Immature cane — very smooth, glabrous.
*Form* (*woody shoot cross section form*).—Circular; pith in center with diaphragm at nodes.
*Color*.—Mature — 5 months, 5GY6/8 (anthocyanins: 5R3/8). Immature — 4 weeks, 5GY4/6 (anthocyanins: 5YR3/4). Dorsal side of internodes — 5GY6/8 (anthocyanins: 5R3/8). Ventral side of internodes — 5GY6/8. Dorsal side of nodes — 5GY6/8 (anthocyanins: 5R3/8). Ventral side of nodes — 5GY6/8.
*Internode length* (*upper mature sun cane*).—13.25 cm.
*Internode width* (*upper mature sun cane*).—12.3 mm.
*Node width*.—15.22 mm.

Bud:

*Bud description*.—Winter bud — rounded, pointed, color 2.5YR4/4. Green bud — rounded and pointed, 5GY6/8 (without anthocyanin coloration).
*Time of bud burst*.—16 February.
*Time of bud leaf burst*.—24 February.

Tendrils:

*Form*.—Mostly trifid.
*Size*.—Medium.
*Length*.—24.8 mm.
*Diameter*.—2.67 mm.
*Texture and distribution of tendril at each node beginning at base*.—Very smooth, discontinuous, 0000000010100101001010010100100 (0 means no tendril at that node and 1 means there is tendril at the node).
*Color*.—Mature — 4 weeks, 2.5GY6/6. Immature — 10 days, 2.5GY5/6.
*Anthocyanin*.—Mature — 2.5YR5/4. Immature — 5R3/6.

Growing tips (young shoot):

*Pubescence*.—Present, very low density of prostrate hairs on the shoot tip.
*Color*.—2.5GY5/8.
*Anthocyanin*.—Absent.
*Shape*.—Fully open.
*Apex*.—Triangular.
*Form of tip*.—Fully open.
*Shoot attitude before tying*.—Semi-erect.

Leaves:

*Shape*.—Pentagonal.
*Apex*.—Pointed.
*Base*.—Pentagonal.
*Number of lobes*.—5.
*Depth of upper lateral sinuses of mature leaves*.—Medium.
*Arrangement of lobes of upper lateral sinuses on mature leaves*.—Slightly.
*Margin*.—Irregular teeth.
*Length of teeth on margin*.—2 to 10 mm.
*Shape of teeth on margin*.—Both sides convex.
*Texture* (*mature leaf*).—Upper surface — smooth, glabrous, without goffering or blistering on upper side of blade. Lower surface — smooth, glabrous.
*Size*.—Immature: Length — 10 days, 4.8 cm. Width — 10 days, 5.4 cm. Mature: Length — 4 weeks, 18 cm. Width — 4 weeks, 16.5 cm. Ratio of length/width of teeth (mature leaf) — medium.
*Color*.—Immature leaf: Upper surface — 5GY4/6 (anthocyanins 5R3/8). Lower surface — 5GY4/6. Mature leaf: Upper surface — 5GY3/4. Lower surface — 5GY5/4. Autumn coloration: Upper surface — 2.5Y7/8. Lower surface — 2.5Y7/6.
*Venation*.—Pattern — palmate (veins on upper leaf are flat; veins on lower leaf are raised), without anthocyanins coloration. Length of middle vein in mature leaves — 12.5 cm.
*Color*.—Upper surface — 2.5GY6/4. Lower surface — 5GY7/6.
*Petiolar sinus*.—Open, lyre shaped, base not limited by veins.
*Petiole*.—Length — 11.3 cm. Diameter — 2.83 mm. Color — 5GY7/8 (anthocyanins 2.5YR5/4).

Floral cluster:

*General description and location*.—Mostly in the 3rd and 4th node, 5% without shoulders.
*Quantity of inflorescences per cluster*.—325.
*Size*.—Length — 14.5 cm. Width — 5.6 cm hanging; 8.6 cm with shoulders spread.
*Peduncle*.—Length — 4.3 cm. Diameter — 3.64 mm.
*Inflorescences*.—Hermaphroditic.

*Stamens*.—5 per flower, straight, 2.76 mm, 5 stamens per flower.

*Anthers*.—Small, nondescript.

*Date of bloom*.—Start: 19 April; 50%: 28 April; 100%: 3 May.

*Pollen amount*.—Sparse.

*Calyptra*.—5 Segments, complete separation.

*Calyptra color*.—5GY5/6.

Fruit:

*Time of year of commercial harvest and shipment*.—Very early season, June 27, in Murcia, Spain.

*Time of beginning of berry ripening*.—Very early.

*Keeping quality*.—After 30 days of cold storage the variety keeps berry firmness, color, and the primary stem looks fresh with green rachis.

*Cluster* (*primary bunches*).—General size — medium (270 g) (450 g tipped and 500 g not tipped). Length (without peduncle) — 19.7 cm tipped and 25 cm not tipped. Width — 10.125 cm hanging, 12.750 cm with shoulders spread. Density — compact. Peduncle length — 3.625 cm. Peduncle diameter — 5.44 mm. Peduncle color — 5GY 7/8. Number of berries per cluster — 80 tipped (on average).

*Berry*.—Size — large (8 g). Diameter — 21.4 mm. Length — 23.6 mm. Shape — broad ellipsoid. Uniformity — very uniform. Brix content — 17° Brix. Titratable acidity — 0.315. Skin color (without bloom) — 2.5GY7/8. Skin color (with bloom) — 2.5GY7/6.

*Pedicel*.—Length — 6.2 mm. Diameter — 1.8 mm. Color — 5GY7/6. Strength of attachment to berry) — very strong.

*Cluster* (*secondary bunches*).—General size — medium, 180 g. Length (without peduncle — 10 cm. Width — 8.6 cm hanging; 10.8 cm with shoulders spread. Density — compact. Peduncle length — 4.5 cm. Peduncle diameter — 3.4 mm. Peduncle color — 5GY7/8. Number of berries per cluster — 32 (on average).

*Berry*.—Size — large, 5.7 g. Diameter — 20.12 mm. Length — 23 mm. Shape — broad ellipsoid. Uniformity — very uniform. Brix content — 18.5° Brix. Titratable acidity — 0.315. Skin color (without bloom) — 2.5GY7/8. Skin color (with bloom) — 2.5GY7/6. Pedicel: Length — 4 mm. Diameter — 1.5 mm. Color — 5GY7/6. Strength of attachment to berry — very strong.

Berry flesh:

*Color*.—2.5GY8/6.

*Juice, color*.—2.5GY7/6.

*Juice production*.—High, 44.2%.

*Thickness of skin*.—Thin.

*Flavor*.—Neutral, fresh.

*Fragrance*.—Neutral.

*Texture*.—Very crunchy (76.5 shores; Shore A scale; 53215 Durometer).

*Seeds*.—Seed rudiments, non-detectable.

*Use*.—Table grape.

Disease and insect resistance: This cultivar is tolerant to one of the main diseases of this species such as *Erysiphe necator*. This cultivar is susceptible to diseases of its species, such as *Plasmopara viticola, Botrytis cinerea, Daktulosphaira vitifoliae, Ceratitis capitata, Planococcus ficus, Planococcus citri, Empoasca vitis*.

What is claimed:

1. A new and distinct variety of grapevine plant named 'BLOMG02' as substantially described and illustrated herein.

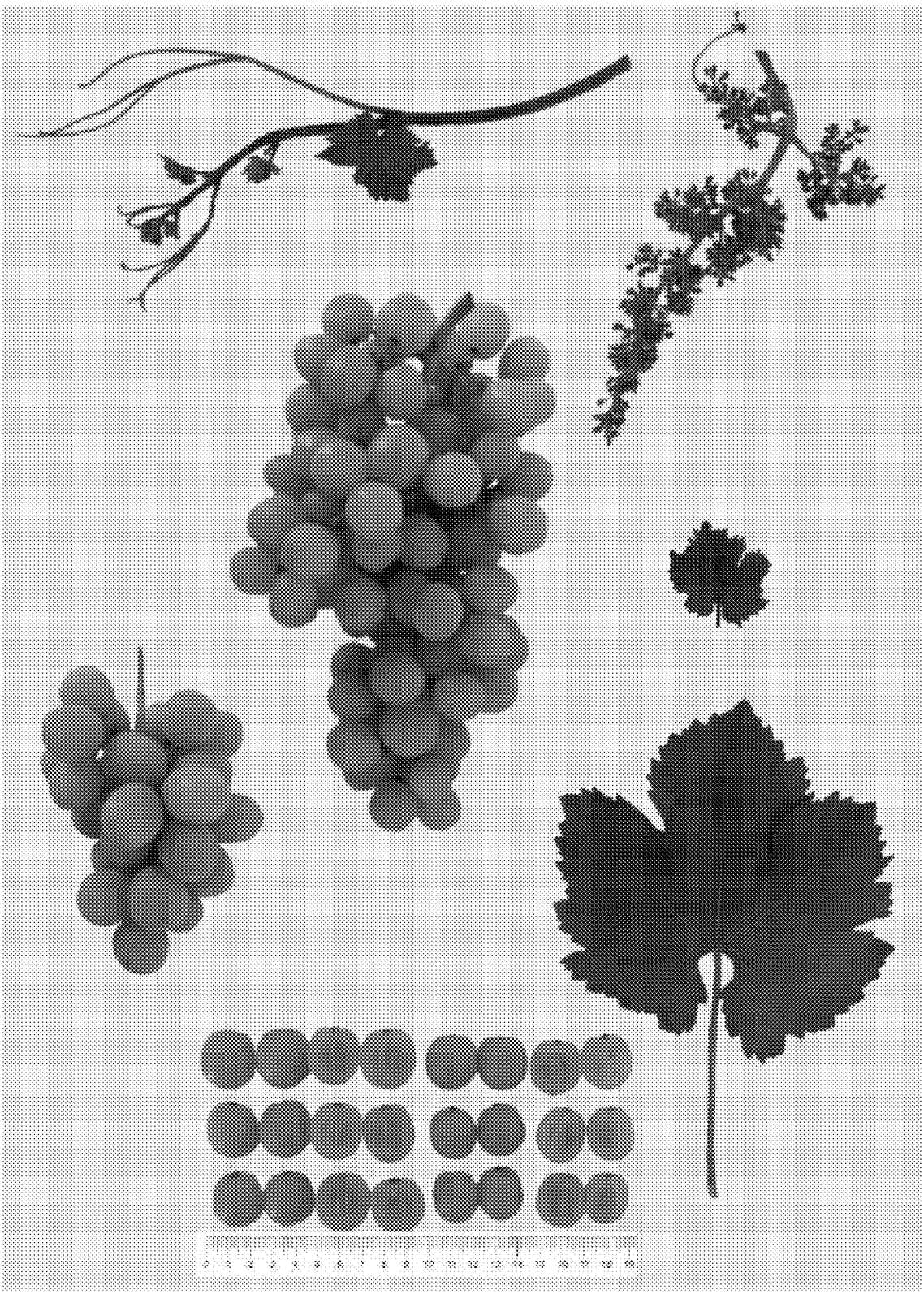

* * * * *